US007316690B2

(12) United States Patent
Parker et al.

(10) Patent No.: US 7,316,690 B2
(45) Date of Patent: Jan. 8, 2008

(54) ANGLED DRIVER WITH DEPTH GAUGE

(75) Inventors: Brad A. Parker, Warsaw, IN (US); Reese K. Myers, Warsaw, IN (US)

(73) Assignee: Symmetry Medical, Inc., Warsaw, IN (US)

( * ) Notice: Subject to any disclaimer, the term of this patent is extended or adjusted under 35 U.S.C. 154(b) by 353 days.

(21) Appl. No.: 11/060,461

(22) Filed: Feb. 17, 2005

(65) Prior Publication Data
US 2006/0184179 A1    Aug. 17, 2006

(51) Int. Cl.
*A61B 17/56* (2006.01)
*A61F 2/00* (2006.01)

(52) U.S. Cl. .................................................. 606/102
(58) Field of Classification Search .............. 606/176, 606/177, 172, 178, 179, 105, 102, 80, 81, 606/82, 83, 84, 85; 408/68
See application file for complete search history.

(56) References Cited

U.S. PATENT DOCUMENTS

| 2,669,162 | A | | 2/1954 | Arliss | 90/17 |
|---|---|---|---|---|---|
| 3,390,596 | A | * | 7/1968 | Trevathan | 408/68 |
| 4,397,593 | A | | 8/1983 | Fordeck | 409/179 |
| 4,406,568 | A | * | 9/1983 | Rogers et al. | 409/182 |
| 5,017,057 | A | * | 5/1991 | Kryger | 408/68 |
| 5,025,548 | A | | 6/1991 | Justesen | 29/560 |
| 5,152,644 | A | * | 10/1992 | Mathews et al. | 409/181 |
| 5,224,803 | A | | 7/1993 | Lallier | 409/131 |
| 5,755,293 | A | | 5/1998 | Bourke | 179/29 |
| 5,863,159 | A | | 1/1999 | Lasko | 408/124 |
| 6,001,115 | A | * | 12/1999 | Ahola et al. | 606/176 |
| 2002/0091392 | A1 | | 7/2002 | Michelson | 606/80 |
| 2003/0061913 | A1 | | 4/2003 | Marquardt | 81/57.3 |
| 2004/0172036 | A1 | * | 9/2004 | Dye | 606/81 |

FOREIGN PATENT DOCUMENTS

DE         003447164 A1    7/1986

* cited by examiner

*Primary Examiner*—Pedro Philogene
(74) *Attorney, Agent, or Firm*—Taylor & Aust, P.C.

(57) ABSTRACT

An angled driver assembly including a rotatable shaft rotatable about a first axis, a rotatable cutting device rotatable about a second axis, the first rotatable portion being coupled to the second rotatable portion, a reference device associated with the rotatable cutting device and an indicator linked to the reference device. The indicator indicates a position of the rotatable cutting device relative to the reference device.

20 Claims, 3 Drawing Sheets

ANGLED DRIVER WITH DEPTH GAUGE

BACKGROUND OF THE INVENTION

1. Field of the Invention

The present invention relates to an orthopeadic driver, and, more particularly, to an offset orthopeadic driven cutting device.

2. Description of the Related Art

An orthopeadic cutter is used to cut a hole in a bone. The cutter may be a drill or a reamer used to cut a bone to a predetermined shape for receiving an orthopeadic implant. For example, an intramedullary reamer may be placed into the intramedullary canal of the bone and used to ream the interior of a bone to receive a stem of an orthopeadic implant. Such a reamer includes a radial peripheral surface which generally includes a plurality of radially extending teeth for cutting the bone in a radial direction as the reamer proceeds in an axial direction in the bone. The size of the opening formed in the bone is determined by the outside diameter of the reamer.

Orthopeadic drills are used to form openings in bones for the receiving of implant devices such as a pin. Drills are rotating devices with a cutting edge for the removal of a portion of the bone.

What is needed in the art is an orthopeadic drill which effectively removes bone to a desired depth.

SUMMARY OF THE INVENTION

The present invention provides an orthopeadic drill driver including an offset driving shaft and an indicator that indicates the depth that a drill extends into a bone.

The invention comprises, in one form thereof, an angled driver assembly including a rotatable shaft rotatable about a first axis, a rotatable cutting device rotatable about a second axis, the first rotatable portion being coupled to the second rotatable portion, a reference device associated with the rotatable cutting device and an indicator linked to the reference device. The indicator indicates a position of the rotatable cutting device relative to the reference device.

An advantage of the present invention is that the surgeon using the device knows the depth that the drill extends into the bone as the drilling operation is underway.

Another advantage of the present invention is that the depth of a blind hole, offset from the observer, is shown on a gauge as bone is being removed.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Figure 1:
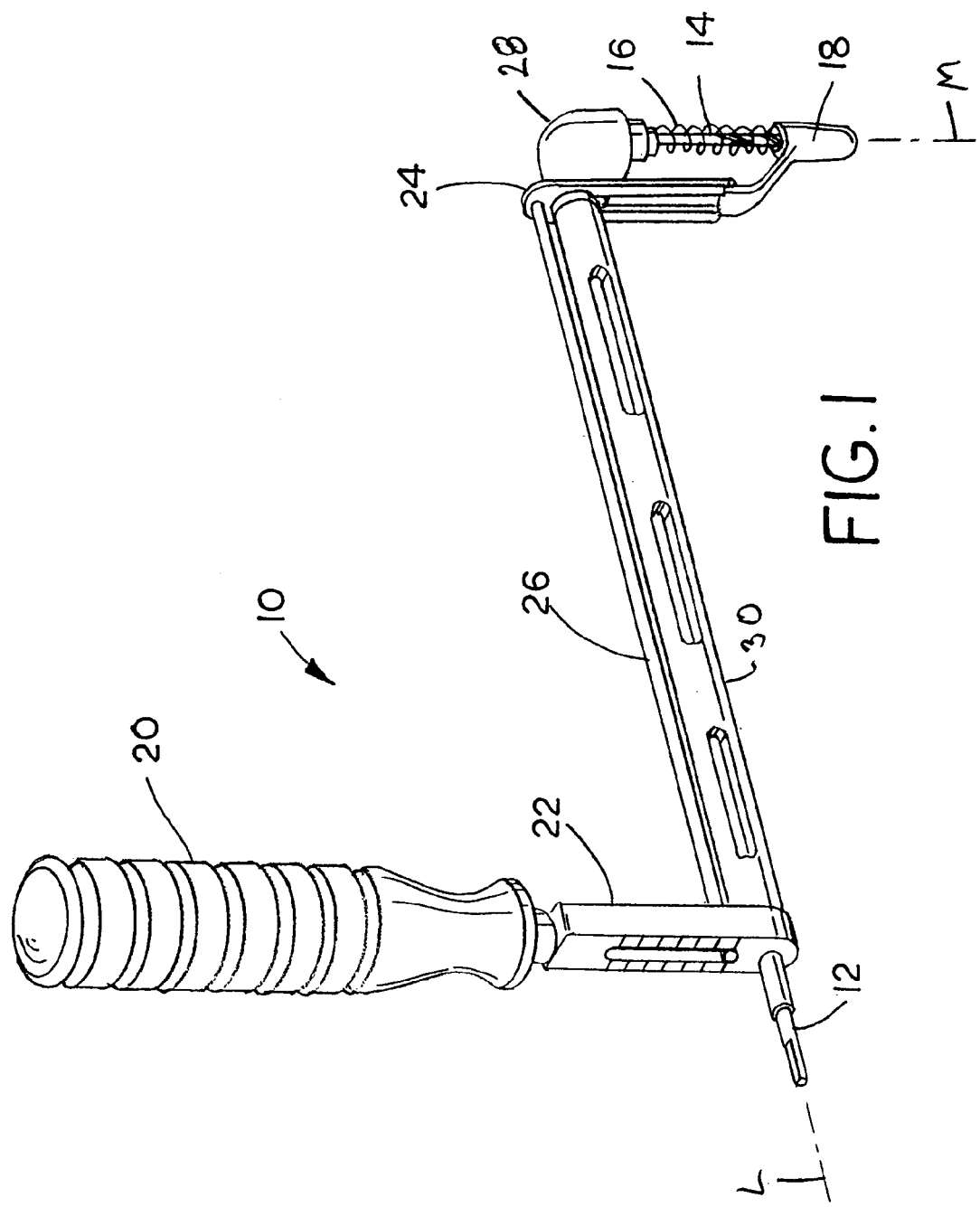
FIG. 1 is a perspective view of an embodiment of an orthopeadic angled driver of the present invention.
Figure 2:
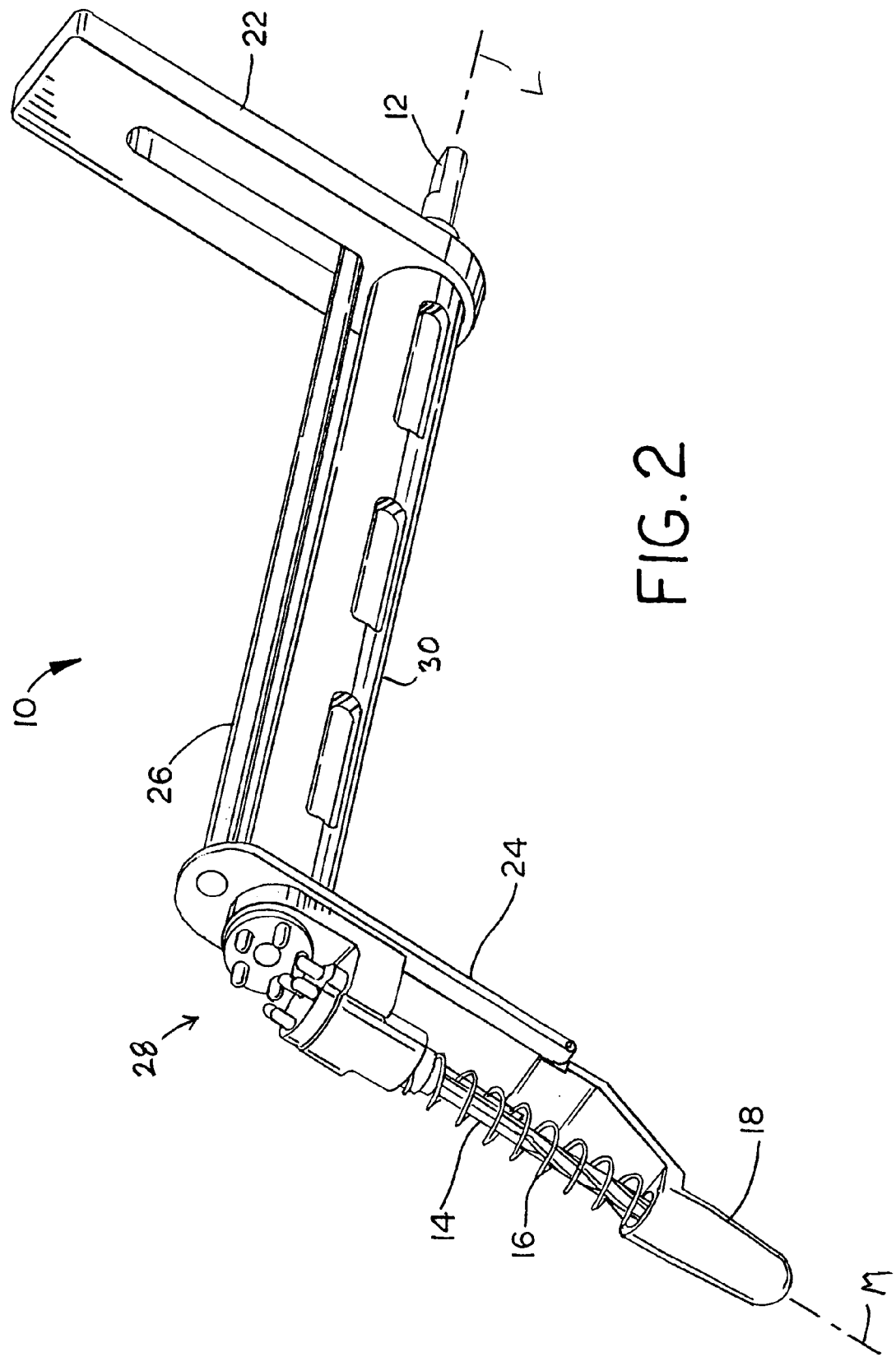
FIG. 2 is another perspective view of the orthopeadic driver of FIG. 1.
Figure 3:
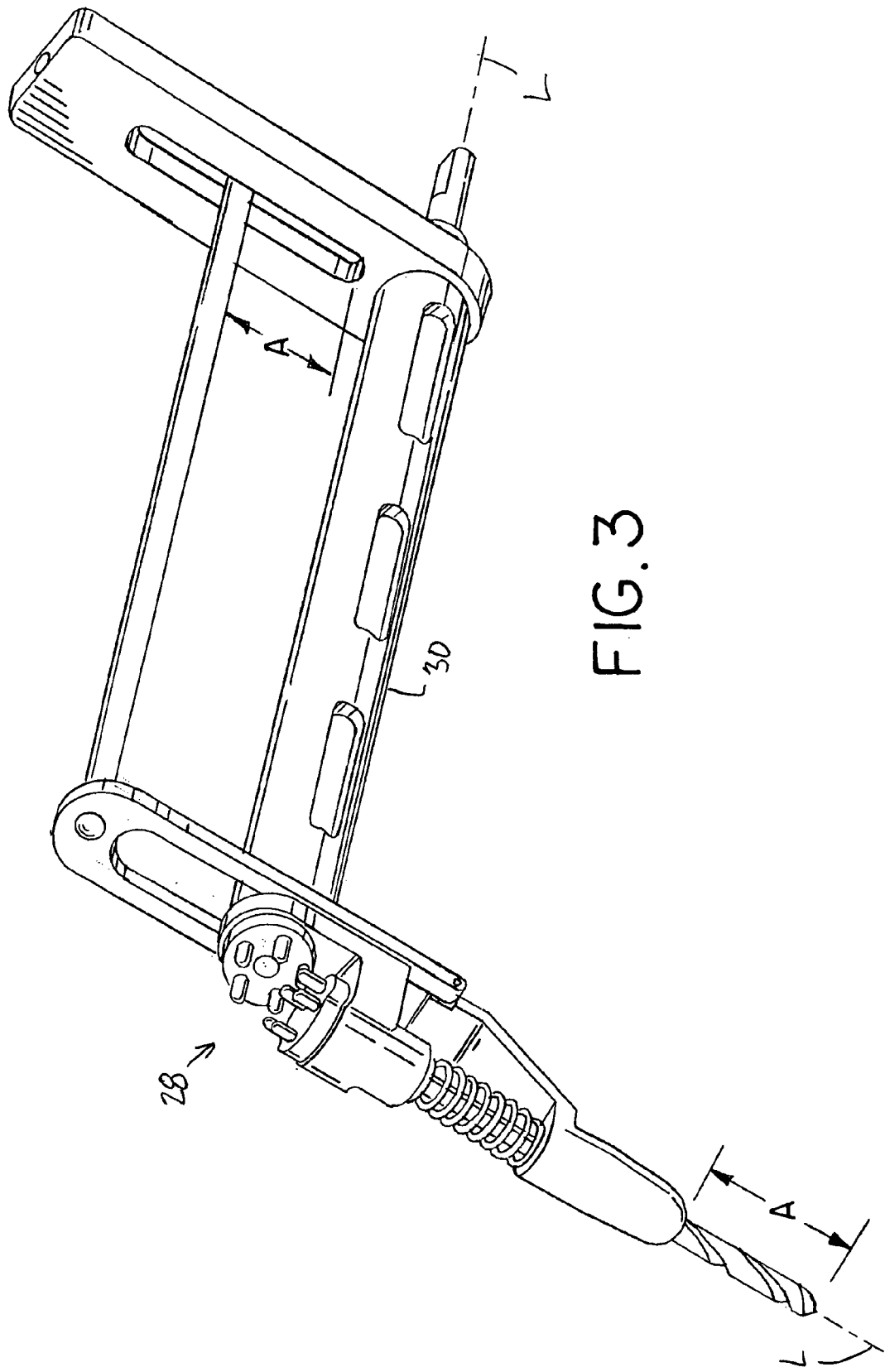
FIG. 3 is yet another perspective view of the orthopeadic driver of FIGS. 1 and 2 showing the cutter in the extended position.

Referring now to the drawings, and more particularly to FIGS. 1-3, there is shown an embodiment of an orthopeadic driver 10 of the present invention, which is used for drilling or reaming bone. Orthopeadic driver 10 includes a rotating driver 12, a cutter 14, a spring 16, a reference device 18, a handle 20, a gauge 22, a linkage 24, an indicator 26, a motion translator 28 and a tube 30.

Rotating driver 12, also known as a rotating shaft 12 rotates about an axis L. One end of rotating shaft 12 is connected to motion translator 28 and another end of rotating shaft 12 is connected to a power device, not shown, for the rotation of rotatable shaft 12. Rotatable shaft 12 transfers motion along its length to motion translator 28. Bearing surfaces within tube 30 may hold rotatable shaft 12 in position relative to tube 30.

Cutter 14 is a rotating cutter, which may be in the form of a drill bit 14, which is connected at one end of motion translator 28. Cutter 14 has cutting edges for the removal of bone when extended beyond reference device 18. Cutter 14 may be in the form of a reamer 14, which is rotatable about an axis M. Axis M is offset from axis L and is, preferably, substantially perpendicular to axis L. Spring 16 biases reference device 18 so that cutter 14 does not extend through reference device 18 until reference device 18 is seated against a portion of bone and the bias of spring 16 is overcome. Reference device 18 has an opening through which cutter 14 extends and is positioned relative to an end of cutter 14 so that when cutter 14 extends a distance A from reference device 18 then its position is indicated by the relative position of indicator 26 to gauge 22. Linkage 24 is connected to reference device 18. Linkage 24 has an extended slot which interacts with a portion of either tube 30 or motion translator 28 to keep reference device 18 axially aligned with cutter 14 as reference device 18 translates along a portion of the length of cutter 14.

Gauge 22 is connected to an end of tube 30 having indicia thereon for indicating the drilling depth of cutter 14 relative to reference device 18. The indicia on gauge 22 may be numeric, color coded or the like to indicate the measured depth of cutter 14. A handle 20 may be connected to a portion of gauge 22 to control the positioning of driver 10 as it is positioned relative to a bone that is to be drilled.

Indicator 26 is shown as a rod-like device attached at one end to linkage 24. Another end of indicator 26 floats in gauge 22 so that the end of indicator 26, proximate to gauge 22, indicates the relative position of linkage 24, which is connected to reference 18, which as a result of its relationship with cutter 14 indicates the depth of cutter 14 as it drills beyond reference device 18.

Motion translator 28 translates the motion of shaft 12, as it rotates about axis L to cutter 14 as it rotates about axis M. Motion translator 28 may include a cog-type arrangement, a beveled-geared arrangement, a worm gear assembly, a flexible shaft or any other known method of translating rotary motion about one axis to rotary motion about another axis. Motion translator 28 has a stationary portion connected to tube 30 and a rotating portion connected to rotatable shaft 12. Motion translator 28 has a second rotating portion connected to cutter 14, thereby transferring motion about axis L to motion about axis M.

As can be seen in FIG. 3, cutter 14 is extended a distance A from reference device 18, which is translated to a movement of indicator 26 by a distance A relative to gauge 22. The movement of cutter 14 corresponds to the movement of indicator 26, thereby showing a surgeon the depth that cutter 14 has extended into the bone. The correspondence between the movement of indicator 26 and the movement of cutter 14 may be a one-to-one relationship as illustrated in FIG. 3. As driver 10 is positioned proximate to the bone, reference device 18 encounters a surface of the bone. As shaft 12 is rotated and longitudinal pressure is applied by way of handle 20 causing cutter 14 to advance and overcome the bias of spring 16, cutter 14 extends through an opening in reference device 18 to begin the cutting operation. When the desired depth is reached, as indicated by the relative position of indicator 26 with gauge 22, the surgeon knows that the desired depth has been reached and pressure is removed as cutting device 14 is retracted back through the opening in reference device 18 and driver 10 is removed from an incision in the patient.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A surgical assembly, comprising:
   a first rotatable portion having a first axis of rotation;
   a second rotatable portion coupled to said first rotatable portion, said second rotatable portion having a second axis of rotation offset from said first axis of rotation;
   a cutting device connected to said second rotatable portion; and
   an indicator proximate said first rotatable portion, said indicator including a floating end displaying a depth said cutting device is extended.

2. The surgical assembly of claim 1, wherein said first axis of rotation is substantially perpendicular to said second axis of rotation.

3. The assembly of claim 1, further comprising a motion translator connected proximate one end of said first rotatable portion, said indicator proximate an other end of said first rotatable portion.

4. The assembly of claim 3, further comprising a gauge having reference indicia thereon, an end of said indicator being proximate said gauge.

5. The assembly of claim 4, further comprising a handle connected proximate said other end of said first rotatable portion.

6. The assembly of claim 4, wherein said cutting device comprises one of a twist drill and a reamer.

7. The assembly of claim 4, further comprising a reference device associated with said cutting device, said reference device having an opening through which said cutting device is extendable.

8. The assembly of claim 7, further comprising a biasing device biasing said cutting device to not extend through said opening in said reference device.

9. The assembly of claim 4, further comprising a tube through which said first rotatable portion extends, said motion translator connected to an end of said tube, said gauge connected to an other end of said tube.

10. The assembly of claim 9, further comprising a handle connected to said gauge.

11. An angled driver assembly, comprising:
    a rotatable shaft rotatable about a first axis;
    a rotatable cutting device coupled with said shaft and rotatable about a second axis;
    a reference device associated with said rotatable cutting device; and
    an indicator linked to said reference device, said indicator including a floating end indicating a position of said rotatable cutting device relative to said reference device.

12. The assembly of claim 11, wherein said first axis and said second axis are substantially perpendicular to each other.

13. The assembly of claim 11, further comprising a motion translator connected proximate one end of said rotatable shaft, said indicator proximate an other end of said rotatable shaft.

14. The assembly of claim 13, further comprising a gauge having reference indicia thereon, an end of said indicator being proximate said gauge.

15. The assembly of claim 14, further comprising a handle connected proximate said other end of said rotatable shaft.

16. The assembly of claim 14, wherein said rotatable cutting device is a twist drill.

17. The assembly of claim 14, wherein said reference device includes an opening through which said cutting device is extendable.

18. The assembly of claim 17, further comprising a biasing device biasing said cutting device to not extend through said opening in said reference device.

19. The assembly of claim 14, further comprising a tube through which said rotatable shaft extends, said motion translator connected to an end of said tube, said gauge connected to an other end of said tube.

20. The assembly of claim 19, further comprising a handle connected to said gauge.

* * * * *